(12) United States Patent
Martin

(10) Patent No.: US 6,562,066 B1
(45) Date of Patent: May 13, 2003

(54) STENT FOR ARTERIALIZATION OF THE CORONARY SINUS AND RETROGRADE PERFUSION OF THE MYOCARDIUM

(76) Inventor: Eric C. Martin, 134 Old Post Rd. North, Croton on Hudson, NY (US) 10520

( * ) Notice: Subject to any disclaimer, the term of this patent is extended or adjusted under 35 U.S.C. 154(b) by 88 days.

(21) Appl. No.: 09/796,528

(22) Filed: Mar. 2, 2001

(51) Int. Cl.[7] .............................. A61F 2/06; A61F 2/04; A61M 5/00
(52) U.S. Cl. .................. 623/1.15; 623/1.13; 623/23.64; 604/8
(58) Field of Search ............................... 623/1.13, 1.14, 623/1.15, 23.64, 23.65, 23.7; 604/8, 96.01

(56) References Cited

U.S. PATENT DOCUMENTS

| | | | |
|---|---|---|---|
| 2,127,903 A | * | 8/1938 | Bowen ........................ 623/1.11 |
| 5,180,392 A | * | 1/1993 | Skeie et al. ............... 623/11.11 |
| 5,287,861 A | | 2/1994 | Wilk |
| 5,380,316 A | | 1/1995 | Aita et al. |
| 5,389,096 A | | 2/1995 | Aita et al. |
| 5,409,019 A | | 4/1995 | Wilk |
| 5,429,144 A | | 7/1995 | Wilk |
| 5,549,581 A | | 8/1996 | Lurie et al. |
| 5,655,548 A | | 8/1997 | Nelson et al. |
| 5,667,486 A | | 9/1997 | Mikulich et al. |
| 5,824,071 A | | 10/1998 | Nelson et al. |
| 5,897,588 A | | 4/1999 | Hull et al. |
| 6,010,530 A | | 1/2000 | Golcoechea |
| 6,015,432 A | * | 1/2000 | Rakos et al. ................ 623/1.15 |
| 6,017,365 A | | 1/2000 | Von Oepen |
| 6,027,526 A | * | 2/2000 | Limon et al. ............... 623/1.15 |
| 6,053,942 A | | 4/2000 | Eno et al. |
| 6,190,406 B1 | | 2/2001 | Duerig et al. |
| 6,258,120 B1 | | 7/2001 | McKenzie et al. |
| 6,371,981 B1 | * | 4/2002 | Yang et al. ................. 623/1.13 |
| 6,395,021 B1 | * | 5/2002 | Hart et al. .................. 623/1.15 |

OTHER PUBLICATIONS

Gensini, G.G., et al., Anatomy of the Coronary Circulation in living Man, Circulation, May 1965, pp. 778–784, vol. XXXI.

Eckstein, R.W., et al., Acute Effects of Elevation of Coronary Sinus Pressure, Circulation, Mar. 1953, pp. 422–436, vol. VII.

Gardner, R.S., et al., Arterialization of Coronary Veins in the Treatment of Myocardial Ischemia, The Journal of Thoracic and Cardiovascular Surgery, Aug. 1974, pp. 273–282, vol. 68, No.2.

Zajtchuk, R., et al., Revascularization of the Heart through the Coronary Veins, The Annals of Thoracic Surgery, Apr. 1976, pp. 318–321, vol. 2, No. 4.

(List continued on next page.)

*Primary Examiner*—Corrine McDermott
*Assistant Examiner*—Alvin Stewart

(57) ABSTRACT

The present invention concerns a novel stent and a method for communicating oxygenated blood directly from the left ventricle to the coronary sinus to provide retrograde perfusion to the myocardium. The stent is placed substantially within the coronary sinus with its trailing end protruding into the right atrium and the leading end protruding into the left ventricle. The stent has a smaller passageway at the trailing (right ventricular) end and at the leading (left ventricle) end, and has a covering at the trailing end. The smaller passageway and the cover at the trailing end to promote retrograde flow into the venous system of the heart and specifically the myocardium of the left ventricle and to reduce a significant left-to-right shunt.

20 Claims, 2 Drawing Sheets

OTHER PUBLICATIONS

Patel, N.H., et al., Percutaneous Transmyocardial Intracardiac Retroperfusion Shunts: Technical Feasibility in a Canine Model, Journal of Vascular and Interventional Radiology, Mar. 2000, pp. 382–390, vol. 11, No. 3.

Rosch, J., et al., Coaxial Catheter–Needle System for Transjugular Portal Vein Entrance, Journal of Vascular and Interventional Radiology, Jan.–Feb. 1993, pp. 145–147, vol. 4.

Schofield, P.M., et al., Transmyocardial Laser Revascularisation in Patients with Refractory Angina: A Randomised Controlled Trail, The Lancet, Feb. 13, 1999, pp. 519–524, vol. 353.

Horvath, K.A., et al., Transmyocardial Laser Revascularization: Results of a Multicenter Trial with Transmyocardial Laser Revascularization Used as Sole Therapy for End–Stage Coronary Artery Disease, The Journal of Thoracic and Cardiovascular Surgery, Apr. 1997, pp. 645–653, vol., 113, No. 4.

Mohl, W., The Momentum of Coronary Sinus Interventions Clinically, Circulation, Jan. 1988, pp. 6–12, vol. 77, No. 1.

Mohl, W., The Relevance of Coronary Sinus Interventions in Cardiac Surgery, Thorac. Cardiovasc. Surgeon, 1991, pp., 245–250, vol. 39.

Kar, S., et al., Coronary Veins: An alternate Route to Ischemic Myocardium, Heart & Lung, Mar. 1992, pp. 148–157, vol. 21, No. 2.

Meerbaum, S., et al., Diastolic Retroperfusion of Acutely Ischemic Myocardium, The American Journal of Cardiology, Mar. 31, 1976, pp. 588–598, vol. 37.

Park, S.B., et al., Direct Selective Myocardial Revascularization by Internal Mammary Artery–Coronary Vein Anastomisis, The Journal of Thoracic and Cardiovascular Surgery, Jan. 1975, pp. 63–72, vol. 69, No. 1.

Hochberg, M.S., Selective Arterialization of the Coronary Venous System, The Journal of Thoracic and Cardiovascular Surgery, Jan. 1979, pp. 1–12, vol. 77, No. 1.

Chiu, C.J., et al., Selective Arterialization of Coronary Veins for Diffuse Coronary Occlusion, The Journal of Thoracic and Cardiovascular Surgery, Jul. 1975, pp. 177–182, vol. 70, No. 1.

Bhayana, J.N., et al., Reversal of Myocardial Ischemia by Arterialization of the Coronary Vein, Jan. 1974, pp. 125–132, vol. 67, No. 1.

Beck, C.S., et al., Scientific Basis for the Surgical Treatment of Coronary Artery Disease, Journal of American Medical Association, Nov. 26, 1955, pp. 1264–1271, vol. 159, No. 13.

Lazar, H.L., Coronary Sinus Interventions during Cardiac Surgery, The Annals of Thoracic Surgery, Oct. 1988, pp. 475–482, vol. 46, No. 4.

Moll, J.W., et al., Arterialization of the Coronary Veins in Diffuse Coronary Arteriosclerosis, J. Cardiovas. Surg., 1975, pp. 520–525, vol. 16.

Beck, C.S., Revascularization of the Heart, Surgery, Jul., 1949, pp. 82–88, vol. 26, No. 1.

Beck, C.S., et al., Operation for Coronary Artery Disease, Journal of American Medical Association, Dec. 29, 1951, pp. 1726–1731, vol. 147, No. .18

Marco, J.D., et al., Coronary Venous Arterialization: Acute Hemodynamic, Metabolic, and Chronic Anatomical Observations, The Annals of Thoracic Surgery, May 1977, pp. 449–454, vol. 23, No. 5.

Beck, C.S., et al., Operations for Coronary Artery Disease, Journal of American Medical Association, Nov. 27, 1954, pp. 1226–1233, vol. 156, No. 13.

Eckstein, R.W., et al., Chronic Effects of Aorta–Coronary Sinus Anastomosis of Beck in Dogs, circulation Research, Jan. 1954, pp. 60–72, vol. 11.

* cited by examiner

STENT FOR ARTERIALIZATION OF THE CORONARY SINUS AND RETROGRADE PERFUSION OF THE MYOCARDIUM

BACKGROUND

1. Field of Invention

The present invention relates to a stent for supplying oxygenated blood retrogradely to the myocardium via the coronary sinus. The stent directs blood from the left ventricle to the coronary sinus through a hole punctured through the wall of the coronary sinus and the wall of the left ventricle and by restricting the outflow of the coronary sinus directs that blood retrogradely.

2. Description of Related Technology

Retrograde perfusion using the coronary sinus has long been known for treating end-stage heart disease. Previous methods among others attempted to connect the aorta to the coronary sinus using a jugular vein or an internal mammary artery graft. These methods were invasive in nature and required open heart surgery.

U.S. Pat. No. 5,824,071, issued to Nelson et al. in 1998, discloses an apparatus and method for providing retrograde perfusion directly from the left ventricle to the coronary sinus. Nelson requires a pressure sensitive valve that prevents pressure build-up inside the coronary sinus from rising above 60 mm Hg. Nelson, however, does not teach how such a valve may be constructed, and it is unlikely that such a device may be introduced percutaneously.

In 2000, Patel et al. conducted experiments for percutaneous arterialization of the coronary sinus using a stent. See Patel et al., *Percutaneous Transmyocardial Intracardiac Retroperfusion Shunts: Technical Feasibility in a Canine Model*, JVIR 2000, 11:382–390. The stent employed by Patel et al., however, results in a significant shunt of oxygenating blood from the left ventricle to the right atrium (hereinafter "left-to-right shunt"). Although Patel recommends using a T or a Y shaped device, technical problems associated with accurately delivering such a device in place render the invention difficult. These factors argue for a simpler device for providing retrograde perfusion to the heart via the coronary sinus.

SUMMARY OF INVENTION

It is an object of the present invention to provide a novel stent and a method for providing oxygenated blood retrogradely from the left ventricle to the heart tissue through the coronary sinus without a significant left-to-right shunt.

In a preferred embodiment, the present invention contemplates a stent having a leading end and a trailing end and having a passageway therethrough. After delivery, the body of the stent is expanded to fit securely within the coronary sinus. The leading end of the stent (hereinafter "leading (LV) end) is positioned in the left ventricle, and the trailing end (hereinafter "trailing (RA) end") is positioned in the right atrium.

The stent has a reduced cross sectional diameter or a smaller passageway at the leading (LV) end and at the trailing (RA) end as compared to the remainder of the stent. The size of the passageway decreases or tapers toward the leading (LV) end and toward the trailing (RA) end. Accordingly, as blood flows into the small passageway of the leading (LV) end, the passageway broadens in diameter toward the midsection of the stent and decreases again toward the small passageway of the training (RA) end.

The smaller passageways at the leading (LV) end and at the trailing (RA) end of the stent operate to control the amount of blood flowing into and out of the coronary sinus. The size of the passageway at the leading (LV) end controls the amount of inflow into the coronary sinus.

The cover surrounding the stent at the trailing (RA) end directs blood flow through the passageway at the trailing (RA) end, and the size of the passageway at the trailing (RA) end controls the amount of outflow into the right atrium. They also control the retrograde flow of oxygenated blood to the myocardium, specifically that of the left ventricle. The stent forms a friction fit with the lumen of the coronary sinus.

The stent has a variable cross-sectional diameter to allow it to be compressed or expanded cross-sectionally. For example, the stent may be compressed cross sectionally to fit within a catheter. After percutaneous delivery into its desired position, the stent may self expand to form a friction fit within the coronary sinus. If a stent does not self expand, it may be expanded using a balloon as known in the art or other suitable mechanism. The present invention also contemplates a heat-dependent expansion stent made of nitinol. The stent is also made of a flexible material that allows bending without forming a kink.

The present invention also contemplates a percutaneous method for delivering and placing a stent of the present invention to allow blood flow from the left ventricle to the coronary sinus. A hole punctured percutaneously through the wall of the coronary sinus and the wall of the left ventricle creates a passageway for flow between the left ventricle and the coronary sinus. The hole is dilated using a balloon as known in the art. After the stent is delivered and positioned between the left ventricle and the right atrium, the sheath of the catheter is removed to expose the stent. Advantageously, the stent forms a friction fit with the interior wall of the coronary sinus as it expands. The trailing (RA) end protrudes through the coronary ostium and extends into the right atrium. The leading (LV) end protrudes through the hole in the wall of the coronary sinus and the wall of the left ventricle to extend into the left ventricle.

In the present invention, the smaller passageway and the cover of the trailing (RA) end restrict blood flow into the right atrium. Pressure inside the coronary sinus is increased, and the blood flows out through the open interstices of the stent retrogradely to perfuse the myocardium.

Some amount of blood flow into the right atrium through the coronary ostium, however, is necessary to control the pressure in the coronary sinus. The diameter of the passageway at the trailing (RA) end should be large enough to prevent the coronary sinus pressure from rising above a suitable pressure, preferably about 50 mm Hg, while reducing a significant amount of left-to-right shunt. It is believed that a suitable pressure limit is such as to avoid damage to the coronary sinus and the left ventricular venous system while effectively providing retrograde perfusion. An optional covering at the leading (LV) end of the stent will depend on stent design. It will help maintain the diameter of the hole in the left ventricular wall.

Thus, the present invention overcomes the difficulty in the prior art with an elegant and simple stent that retrogradely supplies oxygenated blood to the myocardium while decreasing the shunting of oxygenated blood from the left ventricle to the right atrium.

DESCRIPTION OF THE PREFERRED EMBODIMENT OF THE INVENTION

Figure 1:
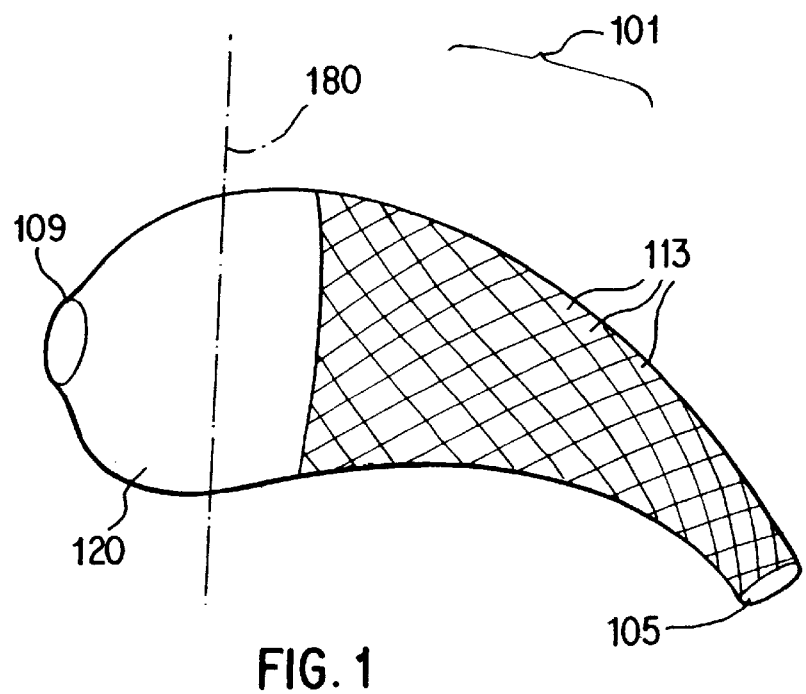
FIG. 1 shows a preferred embodiment of a stent having a wire-mesh construction and the cross sectional area of the stent tapering toward the leading (LV) end and toward the trailing (RA) end, with a covering around the trailing (RA) end.

A preferred embodiment of a stent contemplated in the present invention is illustrated in FIG. 1. An object of the invention is to provide a novel stent 101 which may be placed percutaneously to communicate oxygenated blood from the left ventricle to the coronary sinus. The stent 101 generally comprises a tubular member having a leading (LV) end 105 and a trailing (RA) end 109 and having an axial passageway therethrough.

According to the present embodiment, the stent 101 has relatively smaller passageways or smaller cross sectional diameters at the leading (LV) end 105 and at the trailing (RA) end 109 as compared to the rest of the stent 101. Thus, the cross sectional area of the stent 101 tapers toward the leading (LV) end 105 and toward the trailing (RA) end 109. As blood flows through the stent, the cross sectional area enlarges toward the midsection of the stent 101 and decreases toward the trailing (RA) end 109. The stent 101 at the trailing (RA) end 109 is also surrounded with a cover 120 made of suitable material.

The smaller passageway and the cover at the trailing (RA) end 109 help to direct blood retrogradely and to prevent a significant amount of left-to-right shunt. The smaller passageway of the leading end 105 controls the amount of blood entering the coronary sinus from the left ventricle. A larger passageway at the leading end corresponds to a larger amount of flow, and a smaller passageway corresponds to a smaller amount of flow. As the stent 101 expands to fit securely within the coronary sinus, the cover 120 directs blood flow towards the passageway at the trailing (RA) end 109. By restricting flow into the right atrium, the increased pressure inside the coronary sinus promotes the blood to flow retrogradely to the heart tissue.

Figure 3:
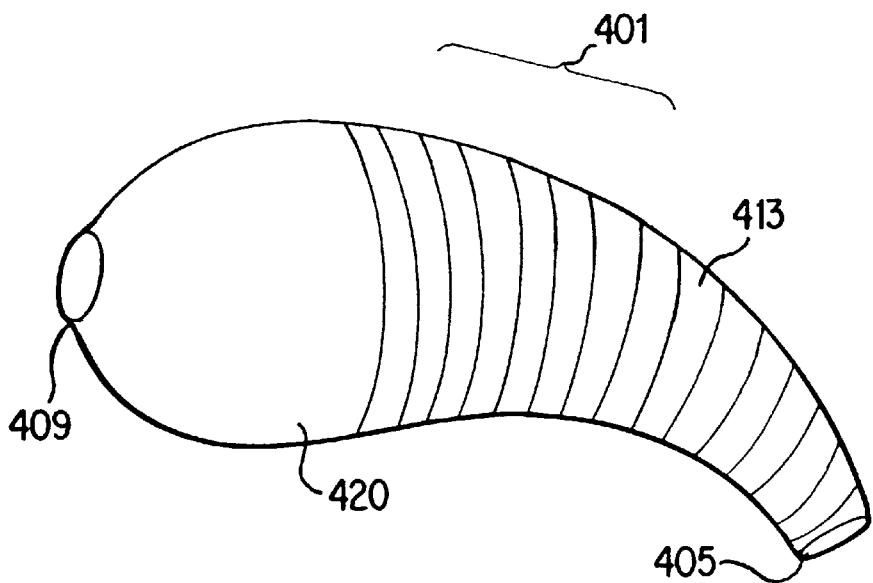
FIG. 3 shows an alternative embodiment of a stent comprising a coiled-type construction.

A number of suitable commercially available stents having the desired characteristics may be employed in practicing the present invention. Generally, the stent 101 has a wire-mesh construction with multiple interstices 113. Numerous variations in wire mesh designs and weave configurations are known in the art. As seen in FIG. 3, the stent 401 may also have a coiled construction with multiple interstices 413. The stent 401 in FIG. 3 also has a leading (LV) end 405 and a trailing (RA) end 409, with the stent 401 tapering toward the leading (LV) end 405 and toward the trailing (RA) and 409.

The stent 101 should also be made of a flexible material that can withstand bending without kinking. The stent 101 should maintain a fluid passageway therethrough to allow sufficient blood flow. The stent 101 may be made of a variety of commercially available materials. Metallic stents as well as non-metallic stents may be used in the construction of the stent 101. Non-metallic stents, for example, may be made of a suitable plastic material. In a preferred embodiment, the stent 101 is made of surgical-grade stainless steel or nitinol.

Figure 2:
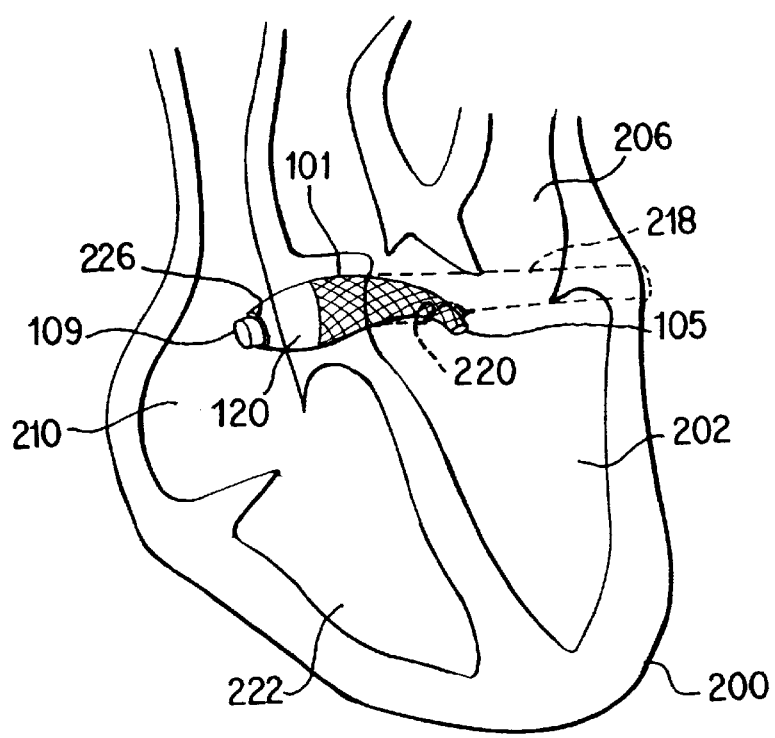
FIG. 2 shows the stent of FIG. 1 in place in a schematic diagram of the human heart.

Referring now to FIG. 2, the stent 101 of FIG. 1 is positioned in a schematic diagram of the human heart 200. The heart 200 generally comprises a left ventricle 202, a left atrium 206, a right ventricle 222, and a right atrium 210. The left ventricle 202 is primarily responsible for delivering oxygenated blood to the body. The left atrium 206 receives the oxygenated blood from the lungs, which is then delivered to the left ventricle 202. The right atrium 210 is primarily responsible for receiving the deoxygenated blood from the body. The deoxygenated blood then flows into the right ventricle 222 before being sent to the lungs for oxygenation.

After perfusing the heart, the deoxygenated blood normally drains through the coronary sinus 218 into the right atrium 210. The coronary ostium 226 separates the right atrium 210 and the coronary sinus 218.

To place the stent, a hole 220 is first punctured percutaneously through the wall of the coronary sinus 218 and the wall of the left ventricle 202 under fluoroscopic control using a stiff needle guide. Access is from the internal jugular vein. The stent may also be marked with appropriate platinum markers to aid fluoroscopic placement. The hole 220 is then widened using a balloon as known in the art or by some other suitable method. In a preferred embodiment, a catheter encasing the compressed stent 101 is introduced and placed into position before removing the sheath to expose the stent 101. The method used by Patel et al., may be employed in delivering the stent according to the present invention. Patel et al., *Percutaneous Transmyocardial Intracardiac Retroperfusion Shunts: Technical Feasibility in a Canine Model*, JVIR 2000, 11:382–390. Patel et al. modifies the stent delivery method as described by Rösch et al. in Rösch et al., *Coaxial Catheter-Needle System for Transjugular Portal Vein Entrance*, JVIR, Volume 4, No. 1. pp. 145–147, 1993.

Referring again to FIG. 1, the stent 101 has variable cross sectional diameter along the tubular member. The diameter of the passageway at the trailing (RA) end 109 is preferably from about 1 mm to about 6 mm, and more preferably from about 2 mm to about 4 mm. Likewise, the diameter of the passageway at the leading (LV) end 105 is preferably from about 1 mm to about 6 mm, and more preferably from about 2 mm to about 5 mm. The cross sectional area increases from the leading (LV) end 105 to the midsection of the stent and decreases again toward the trailing (RA) end 109. The diameter of the cross sectional area at plane 180, which is the largest cross sectional area of the stent 101, is preferably from about 7 mm to about 12 mm. The passageway therefore tapers toward each end 109 or 105.

Referring now to FIG. 2, the stent 101 is positioned as follows. The stent 101 is positioned to fit substantially within the coronary sinus 218 to form a friction fit. The leading (LV) end 105 of the stent 101 protrudes through the hole 220 and extends into the left ventricle 202. The leading (LV) end 105 extends preferably from about 2 mm to about 5 mm into the left ventricle 202. The trailing (RA) end 109 of the stent 101 protrudes past the coronary ostium 226 into the right atrium 210. The trailing (RA) end 109 protrudes preferably from about 2 mm to about 10 mm into the right atrium 210. An optional cover (not shown) may also be placed around the leading (LV) end 105 to guarantee the inflow diameter.

As discussed, a cover 120 surrounds the stent 101 near the trailing (RA) end 109. As blood flows from the coronary sinus 218 towards the right atrium 210, the cover directs the blood into the right atrium 210 through the passageway at the trailing (RA) en 109. Thus, the cover 120 helps in controlling the amount of blood flow through the coronary ostium 226. The cover 120 is preferably made of a number of commercially available materials, such as PET, PTFE, etc. The cover 120 preferably covers from about 0.5 cm to about 2 cm of the trailing end 109 of the stent 101, and more preferably from about 1 cm to about 2 cm of the trailing (RA) end 109 of the stent 101. Blood flowing from the left ventricle 202 into the coronary sinus 218 is also directed through the interstices 113 in the stent 101 to provide retrograde perfusion to the myocardium because of the increased coronary sinus pressure caused by the small passageway at the trailing (RA) end.

Blood flowing through the coronary ostium 226 is also controlled by controlling the size of passageway at the leading (LV) end 105. If the flow rate through the passageway at the trailing (RA) end 109 is too great, the heart tissue would not adequately be perfused and there would be a large left-to-right shunt. If, however, the size of the passageway at the trailing (RA) end 109 is too small, pressure build up within the coronary sinus 218 would damage the venous system being perfused retrogradely. Preferably, the pressure within the coronary sinus should not exceed a suitable pressure range to avoid damage to the coronary sinus venous system. For example, the pressure should not exceed approximately 50 mm Hg. Thus, the passageway at the trailing (RA) end 109 should be large enough to prevent excess pressure build up, but restrictive enough to allow the heart to be supplied with oxygenated blood.

Coronary sinus pressure may also be controlled by controlling the amount of blood flowing from the left ventricle 202 into the coronary sinus 218. Thus, the size of the passageway at the leading (LV) end 105 may be controlled in relation to the size of the passageway at the trailing (RA) end 109 to provide efficient retrograde perfusion of heart tissue without excessive pressure build up.

Figure 4:
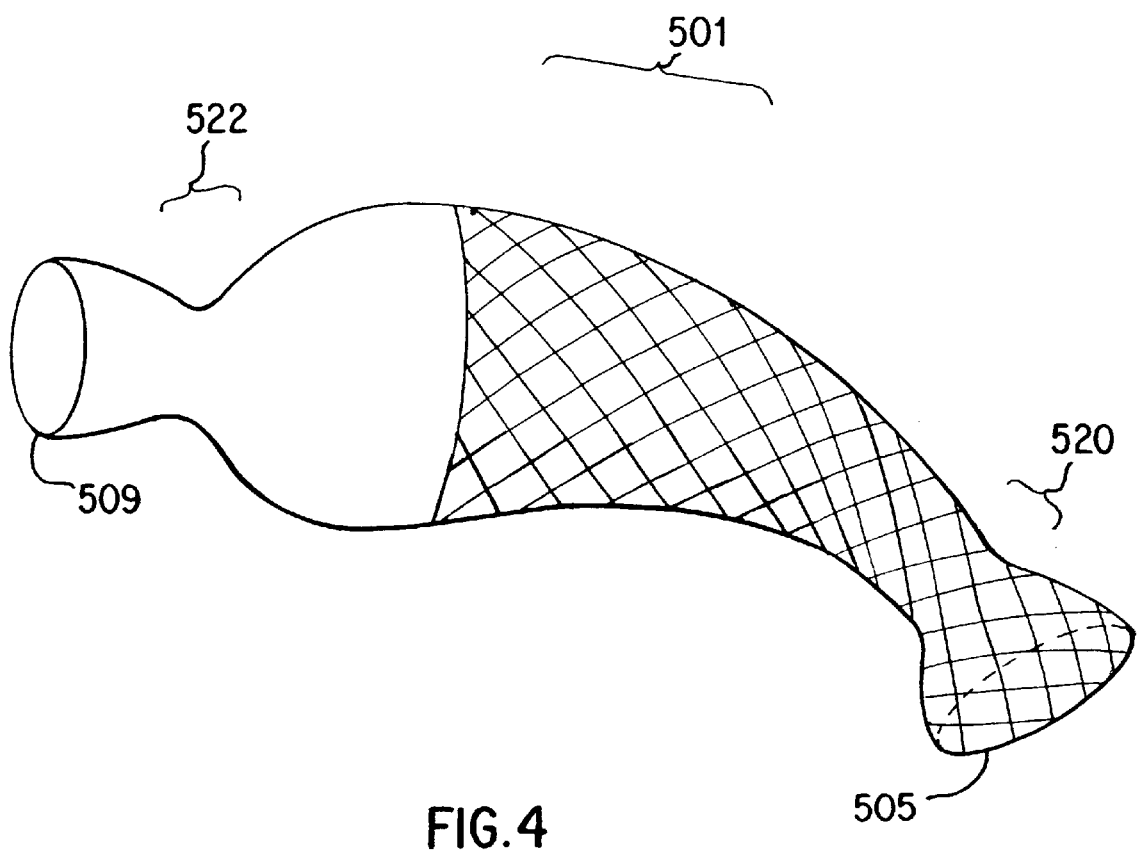
FIG. 4 shows an alternative embodiment of a stent having flaring ends with constrictions near the trailing end and the leading end.

In an alternative embodiment, as seen in FIG. 4, the smallest cross sectional areas of the stent 501 may not be at the leading (LV) end 505 and the trailing (RA) end 509, but may be approximately 1 mm to about 1 cm from the leading (LV) end 505 and the trailing (RA) end 509. Thus, the stent 101 would have one or two flaring ends. The smallest cross sectional area would be at constriction 520, which is near the leading (LV) end 505, and at constriction 522, which is near the trailing (RA) end 509.

I claim:

1. A stent for supplying oxygenated blood to heart tissue retrogradely through the coronary sinus comprising:
   a tubular member having a leading end and a trailing end and a passageway therethrough,
   said tubular member having one or more interstices therein,
   wherein cross sectional area of said tubular member varies along its extent,
   said tubular member tapering cross sectionally toward the leading end and toward the trailing end, and
   said tubular member surrounded by a cover near the trailing end.

2. The stent according to claim 1, wherein diameter of the cross sectional area at the trailing end controls the amount of blood flow into the right atrium.

3. The stent according to claim 1, wherein diameter of the cross sectional area at the trailing end provides retrograde perfusion while maintaining an appropriate pressure within the coronary sinus.

4. The stent of claim 3, wherein said appropriate pressure is approximately 50 mm Hg.

5. The stent according to claim 1, wherein diameter of the cross sectional area at the trailing end is from about 1 mm to about 6 mm.

6. The stent according to claim 1, wherein diameter of the cross sectional area at the trailing end is from about 2 mm to about 4 mm.

7. The stent according to claim 1, wherein diameter of the cross sectional area at the leading end controls the amount of blood flowing into the stent.

8. The stent according to claim 1, wherein diameter of the cross sectional area at the leading end is from about 1 mm to about 6 mm.

9. The stent according to claim 1, wherein diameter of the cross sectional area at the leading end is from about 2 mm to about 5 mm.

10. The stent according to claim 1, wherein diameter of the cross sectional area is variable to allow compression and expansion.

11. The stent according to claim 1, wherein said tubular member is flexible to allow bending.

12. The stent according to claim 1, wherein said stent has a mesh construction.

13. The stent according to claim 1, wherein said stent has a coiled construction.

14. The stent according to claim 1, wherein diameter of the cross sectional area does not exceed from about 6 mm to about 12 mm.

15. The stent according to claim 1, wherein said cover surrounds from about 0.5 cm to about 2 cm of the stent at the trailing end.

16. The stent according to claim 1, wherein said cover surrounds from about 1 cm to about 2 cm of the stent at the trailing end.

17. The stent according to claim 1, wherein said stent has a cover surrounding the stent at the leading end.

18. The stent according to claim 17, wherein said cover surrounds from about 0.5 cm to about 2 cm of the stent at the leading end.

19. A stent for supplying oxygenated blood to heart tissue retrogradely through the coronary sinus comprising:
   a tubular member having a leading end and a trailing end and a passageway therethrough,
   said tubular member having one or more interstices therein,
   wherein cross sectional area of said tubular member varies along its extent,
   said tubular member tapering having a constriction near the leading end and a constriction near the trailing end, and
   said tubular member surrounded by a cover near the trailing end.

20. A stent for supplying oxygenated blood to heart tissue retrogradely through the coronary sinus comprising:
   a tubular member having a leading end and a trailing end and a passageway therethrough,
   said tubular member having one or more interstices therein,
   wherein cross sectional area of said tubular member varies along its extent, and
   said tubular member surrounded by a cover near the trailing end,
   wherein diameter of the cross sectional area at the trailing end maintains pressure in the coronary sinus to provide retrograde perfusion to the myocardium while avoiding damage to the venous system.

* * * * *